(12) United States Patent
Eckhardt et al.

(10) Patent No.: US 8,231,679 B2
(45) Date of Patent: Jul. 31, 2012

(54) PROSTHESIS CONNECTION MECHANISM (75) Inventors: Jason John Eckhardt, Memphis, TN (US); Vincent C. Traynelis, Chicago, IL (US); J. Kenneth Burkus, Columbus, GA (US); Regis W. Haid, Jr., Atlanta, GA (US)

(73) Assignee: Warsaw Orthopedic, Warsaw, IN (US)

( * ) Notice: Subject to any disclaimer, the term of this patent is extended or adjusted under 35 U.S.C. 154(b) by 245 days.

(21) Appl. No.: 12/693,155

(22) Filed: Jan. 25, 2010

(65) Prior Publication Data

US 2011/0184521 A1    Jul. 28, 2011

(51) Int. Cl.
*A61F 2/44* (2006.01)

(52) U.S. Cl. ............... 623/17.16; 623/17.11; 623/17.15; 606/249

(58) Field of Classification Search .......... 606/246–249; 623/17.11–17.16

See application file for complete search history.

(56) References Cited

U.S. PATENT DOCUMENTS

2005/0085913 A1 * 4/2005 Fraser et al. ............... 623/17.11

* cited by examiner

*Primary Examiner* — Eduardo C Robert
*Assistant Examiner* — Christina Negrelli (57) ABSTRACT A prosthesis comprising a component for engaging a surface of a vertebral body is disclosed. The component comprises a bone-engaging surface and an outer surface that is not bone-engaging, wherein the bone-engaging surface is configured to engage a portion of the surface of the vertebral body, wherein the vertebral body has been configured to engage with the bone-engaging surface, and wherein after the component is engaged with the vertebral body, at least at a location of an area of a junction between a vertical surface and an endplate surface of the vertebral body, the outer surface of the component has a shape that is substantially similar to an anatomical shape of the vertebral body.

18 Claims, 9 Drawing Sheets

PROSTHESIS CONNECTION MECHANISM

FIELD OF INVENTION

The present invention is directed to systems or mechanisms for affixing a prosthesis or portion of a prosthesis to bone.

BACKGROUND

The present disclosure relates to mechanisms for affixing prostheses to bone, and more particularly, systems for affixing at least a portion of a prosthesis to bone.

SUMMARY OF THE INVENTION

A prosthesis comprising a component for engaging a surface of a vertebral body is disclosed. The component comprises a bone-engaging surface and an outer surface that is not bone-engaging, wherein the bone-engaging surface is configured to engage a portion of the surface of the vertebral body, wherein the vertebral body has been configured to engage with the bone-engaging surface, and wherein after the component is engaged with the vertebral body, at least at a location of an area of a junction between a vertical surface and an endplate surface of the vertebral body, the outer surface of the component has a shape that is substantially similar to an anatomical shape of the vertebral body.

Additional aspects and features of the present disclosure will be apparent from the detailed description and claims as set forth below.

DETAILED DESCRIPTION

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
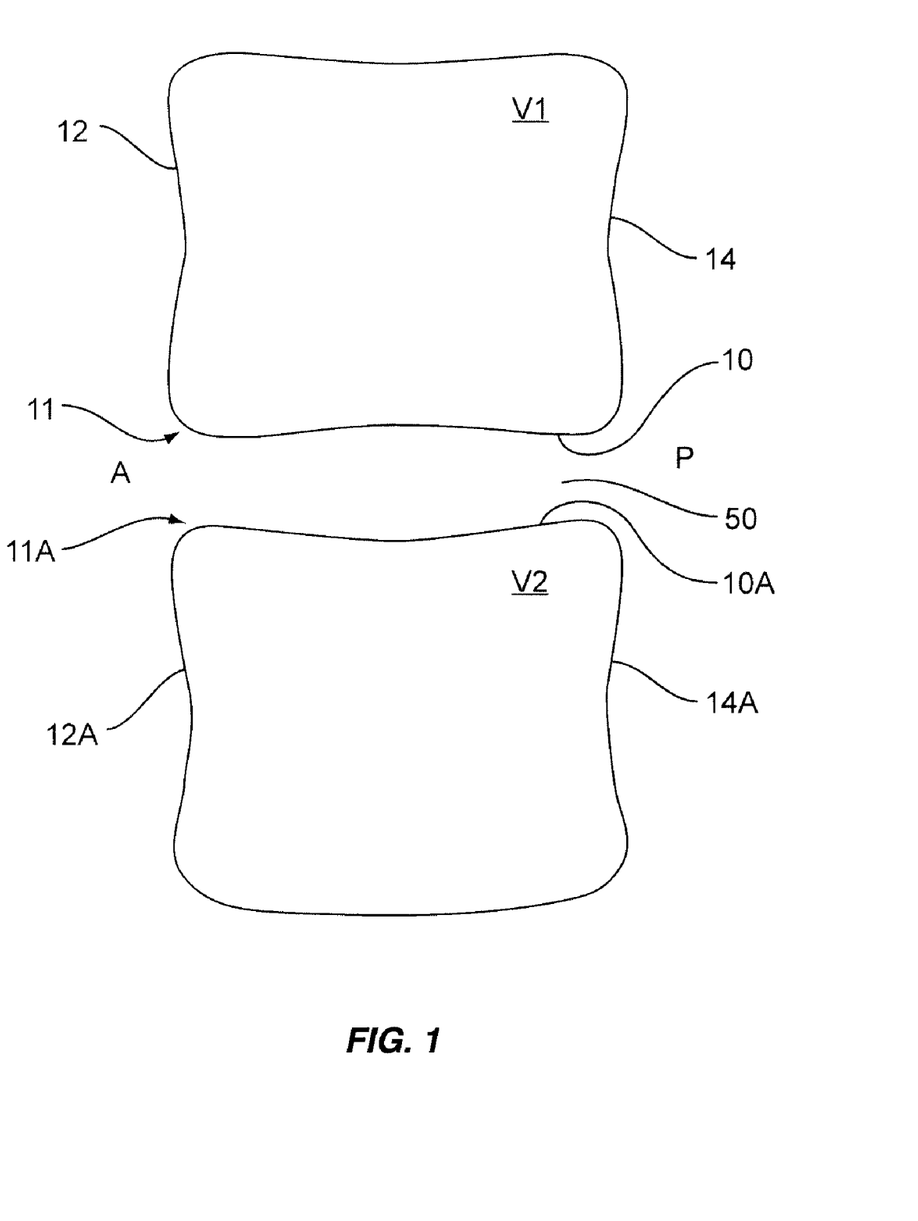
FIG. 1 shows a schematic, cross-sectional view of two adjacent vertebral bodies after a disc situated between the two has been removed.

FIG. 1 shows a schematic, cross-sectional view of two adjacent vertebral bodies V1 and V2 after a disc situated between the two is removed. FIG. 1 depicts a superior vertebral body V1, an inferior vertebral body V2, and a disc space 50 between the two vertebral bodies V1 and V2. Reference marker A represents an anterior side of the vertebral bodies V1 and V2, whereas reference marker P represents a posterior side of the vertebral bodies V1 and V2. As shown in FIG. 1, superior vertebral body V1 has an anterior vertical surface 12, a posterior vertical surface 14, an endplate surface 10, and a junction 11 between the vertical surface 12 and the endplate surface 10. Similarly, as shown in FIG. 1, inferior vertebral body V2 has an anterior vertical surface 12A, a posterior vertical surface 14A, an endplate surface 10A, and a junction 11A between the vertical surface 12A and the endplate surface 10A. FIG. 1 shows a schematic, cross-sectional view of an anatomical shape of the vertebral body V1.

Figure 2:
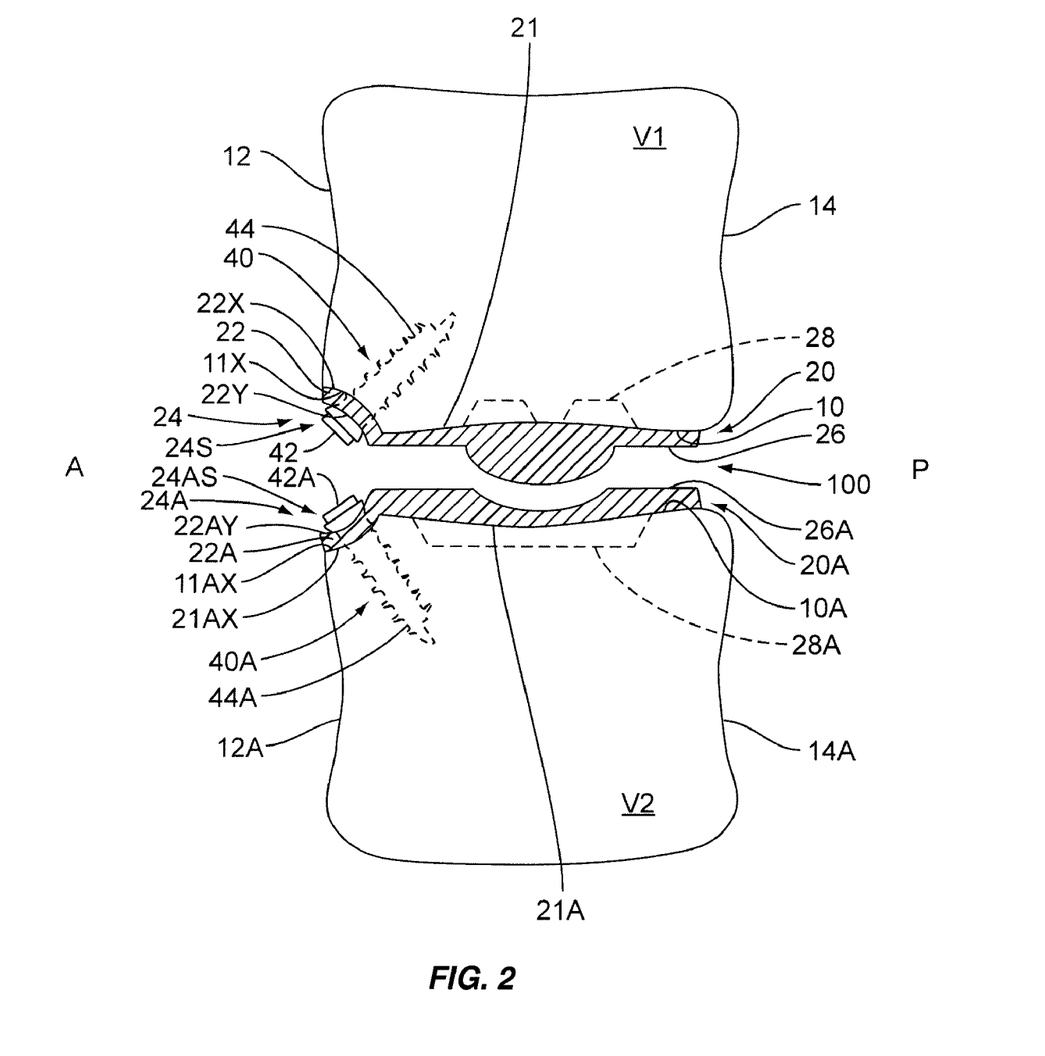
FIG. 2 is a schematic, cross-sectional view of a prosthesis in a sagittal plane.

FIG. 2 shows a schematic, cross-sectional view of a prosthesis 100 in a sagittal plane, situated primarily in the disc space 50 between vertebral bodies V1 and V2. Reference marker A represents an anterior side of the vertebral bodies V1 and V2, whereas reference marker P represents a posterior side of the vertebral bodies V1 and V2. The prosthesis 100 comprises a component 20 for engaging a surface of a vertebral body V1. The component 20 comprises a bone-engaging surface 21 and an outer surface 26 that is not bone-engaging, wherein the bone-engaging surface 21 is configured to engage a portion of the surface of the vertebral body V1, wherein the vertebral body V1 has been configured to engage with the bone-engaging surface 21. After the component 20 is engaged with the vertebral body V1, at least at a location of an area 24 of the junction 11 between the vertical surface 12 and the endplate surface 10 of the vertebral body V1, an outer surface 24S at area 24 of the component 20 has a shape that is substantially similar to an anatomical shape of the vertebral body V1. An anatomical shape of junction 11 is shown in FIG. 1. Note that component 20 comprises portion 22 that is situated at the location of junction 11, and the area where portion 22 engages the vertebral body V1 is labeled by reference marker 24.

The term "substantially" (or "substantial") as used herein may be applied to modify any quantitative representation which could permissibly vary without resulting in a change in the basic function to which it is related. For example, while the outer surface 24AS of the component 20 is not necessarily identical to an anatomical shape of junction 11 of vertebral body V1, it is substantially similar. Specifically, system 100 is designed so that component 20 or other parts of the prosthesis 100 at least at a location of area 24 of junction 11 do not interfere, or if any, provide minimal interference with existing tissue at the location of junction 11.

As shown in FIG. 2, at the junction 11 between the vertical surface 12 and the endplate surface 10 of the vertebral body V1, the bone-engaging surface 21 of the component 20 has a cross-sectional shape in a sagittal plane that comprises a convex shape 22X, and the vertebral body V1 has a concave shape 11X at the same area 24 to engage with the surface 22X. Note that the outer surface of component 20 at portion 22 is labeled by reference marker 22Y. As shown in FIG. 2, outer surface 22Y has a concave shape.

Also, as shown in FIG. 2, the prosthesis 100 further comprises a component 20A for engaging a surface of a vertebral body V2. The component 20A comprises a bone-engaging surface 21A and an outer surface 26A that is not bone-engaging, wherein the bone-engaging surface 21A is configured to engage a portion of the surface of the vertebral body V2, wherein the vertebral body V2 has been configured to engage with the bone-engaging surface 21A. After the component 20A is engaged with the vertebral body V2, at least at a location of an area 24A of junction 11A between the vertical surface 12A and the endplate surface 10A of the vertebral body V2, an outer surface 24AS at area 24A of the component 20A has a shape that is substantially similar to an anatomical shape of the vertebral body V2. An anatomical shape of junction 11A is shown in FIG. 1. Note that component 20A comprises portion 22A that is situated at the location of junction 11A, and the area where portion 22A engages the vertebral body V2 is labeled by reference marker 24A.

Also, similar to component 20, as shown in FIG. 2, component 20A and vertebral body V2 have similar configurations at the junction 11A between the vertical surface 12A and the endplate surface 10A of the vertebral body V2. That is, the bone-engaging surface 21A of the component 20A has a cross-sectional shape in a sagittal plane that comprises a convex shape 21AX, and the vertebral body V1 has a concave shape 11AX at the same area 24A to engage with surface 21AX. Note that the outer surface of component 20 at portion 22 is labeled by reference marker 22AY. Also, as shown in FIG. 2, outer surface 22AY has a concave shape.

Also, as shown in FIG. 2, a fastener 40 is used to affix part 22 of component 20 to the area 24 of junction 11 of vertebral body V1. Fastener 40 has a distal end 44 and a fastener head 42. As shown in FIG. 2, after the component 20 is engaged with the vertebral body V1 and fastener 40 is inserted in its intended final position, at the area 24 of junction 11 between the vertical surface 12 and the endplate surface 10 of the vertebral body V1 where the head 42 of fastener 40 is located, an outer surface 24S at area 24 of the head 42 of the fastener 40 in combination with the outer surface of component 20 has a shape that is substantially similar to an anatomical shape of the vertebral body V1. FIG. 2 shows fastener 40 in its intended final position, where as shown, the head 42 contacts the outer surface 22Y of component 20.

Similarly, as shown in FIG. 2, a fastener 40A is used to affix part 22A of component 20A to the area 24A of junction 11A of vertebral body V2. Fastener 40A has a distal end 44A and a fastener head 42A. As shown in FIG. 2, after the component 20A is engaged with the vertebral body V2 and fastener 40A is inserted in its intended final position, at the area 24A of junction 11A between the vertical surface 12A and the endplate surface 10A of the vertebral body V2 where the head 42A of fastener 40A is located, an outer surface 24AS at area 24A of the head 42A of the fastener 40A in combination with the outer surface of component 20A has a shape that is substantially similar to an anatomical shape of the vertebral body V2. FIG. 2 shows fastener 40A in its intended final position, where as shown, the head 42A contacts the outer surface 22AY of component 20A. Fastener 40 and/or fastener 40A may be any device to help affix their respective components to the respective vertebral bodies, for example, a screw.

Also, as shown in FIG. 2, component 20 may further comprise structures 28 to help affix component 20 to vertebral body V1. Structures 28 may be anchors, keels, spikes, pegs, prongs, or similar structures to help component 20 affix to vertebral body V1. Similarly, component 20A may further comprise structures 28A to help affix component 20A to vertebral body V2. Structures 28A may be anchors, keels, spikes, pegs, prongs, or similar structures to help component 20A affix to vertebral body V2. Surface coatings such as Hydroxyapatite (HA), plasma spray or beading also may be used instead of or in addition to respective structures 28 and 28A to help affix components to their respective vertebral bodies.

Figure 2A:
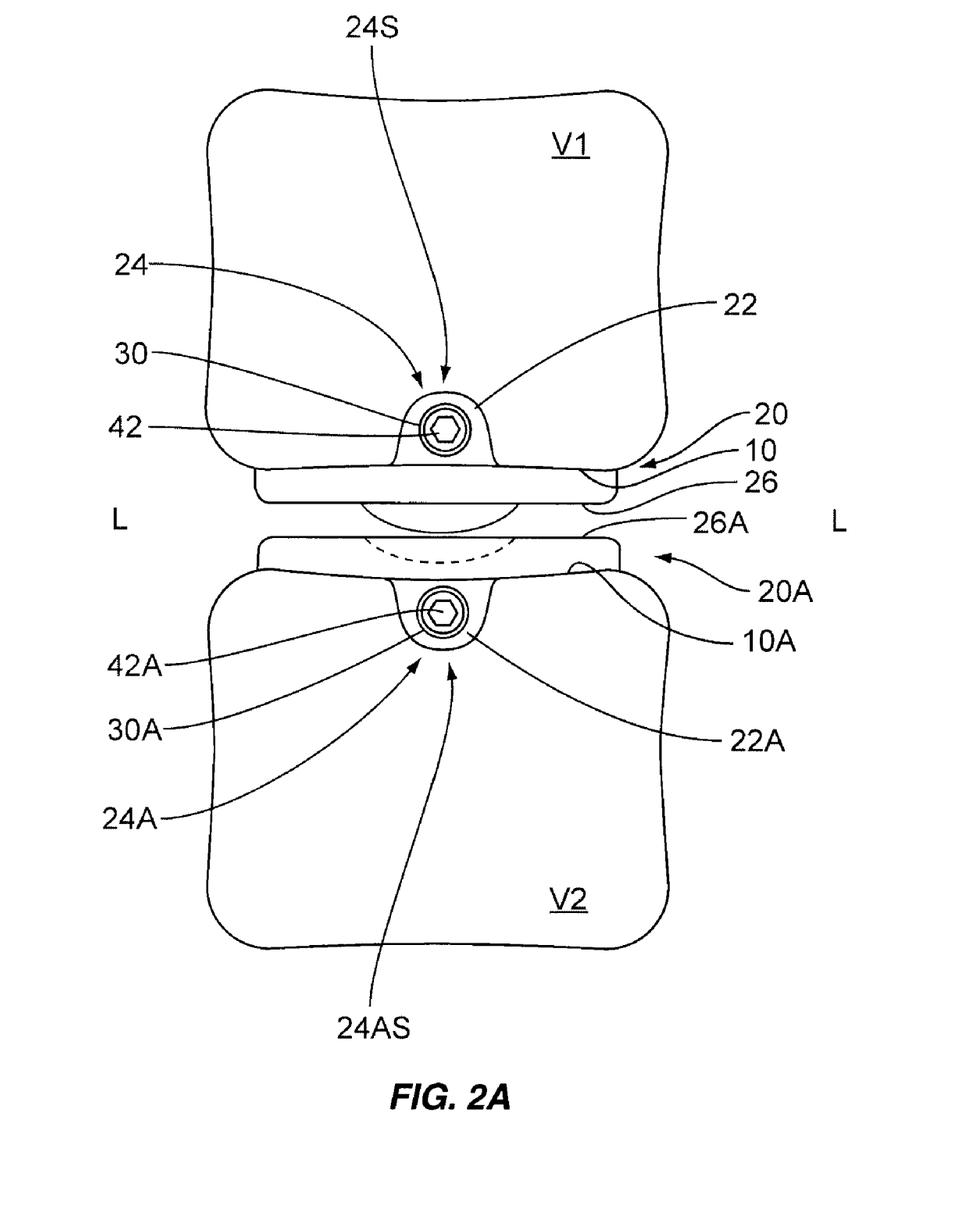
FIG. 2A is a frontal view of the prosthesis of FIG. 2, i.e., a view from the anterior side of vertebral bodies V1 and V2.

FIG. 2A shows a frontal view of prosthesis 100 of FIG. 2. This view is from the anterior side of vertebral bodies V1 and V2, where reference marker L represents lateral sides of vertebral bodies V1 and V2. As shown in FIG. 2A, component 20 comprises a single portion 22 that is situated at the location of junction 11, and the area where portion 22 engages the vertebral body V1 is labeled by reference marker 24. Portion 22 provides an area 24 for helping component 20 affix to vertebral body V1. Further, as shown, portion 22 comprises a fastener-receiving hole 30 configured to receive fastener 40 and for allowing fastener 40 to engage the vertebral body V1. As shown in FIG. 2, the fastener-receiving hole 30 is configured to allow the fastener 40 to engage the vertebral body V1 in a direction toward the substantial center of the vertebral body V1. As shown in the frontal view of FIG. 2A, fastener head 42 is visible.

Similarly, as shown in FIG. 2A, component 20A comprises a single portion 22A that is situated at the location of junction 11A, and the area where portion 22A engages the vertebral body V2 is labeled by reference marker 24A. Portion 22A provides an area 24A for helping component 20A affix to vertebral body V2. Further, as shown, portion 22A comprises a fastener-receiving hole 30A configured to receive fastener 40A and for allowing fastener 40A to engage the vertebral body V2. As shown in FIG. 2, the fastener-receiving hole 30A is configured to allow the fastener 40A to engage the vertebral body V2 in a direction toward the substantial center of the vertebral body V2. As shown in the frontal view of FIG. 2A, fastener head 42A is visible.

Figure 2B:
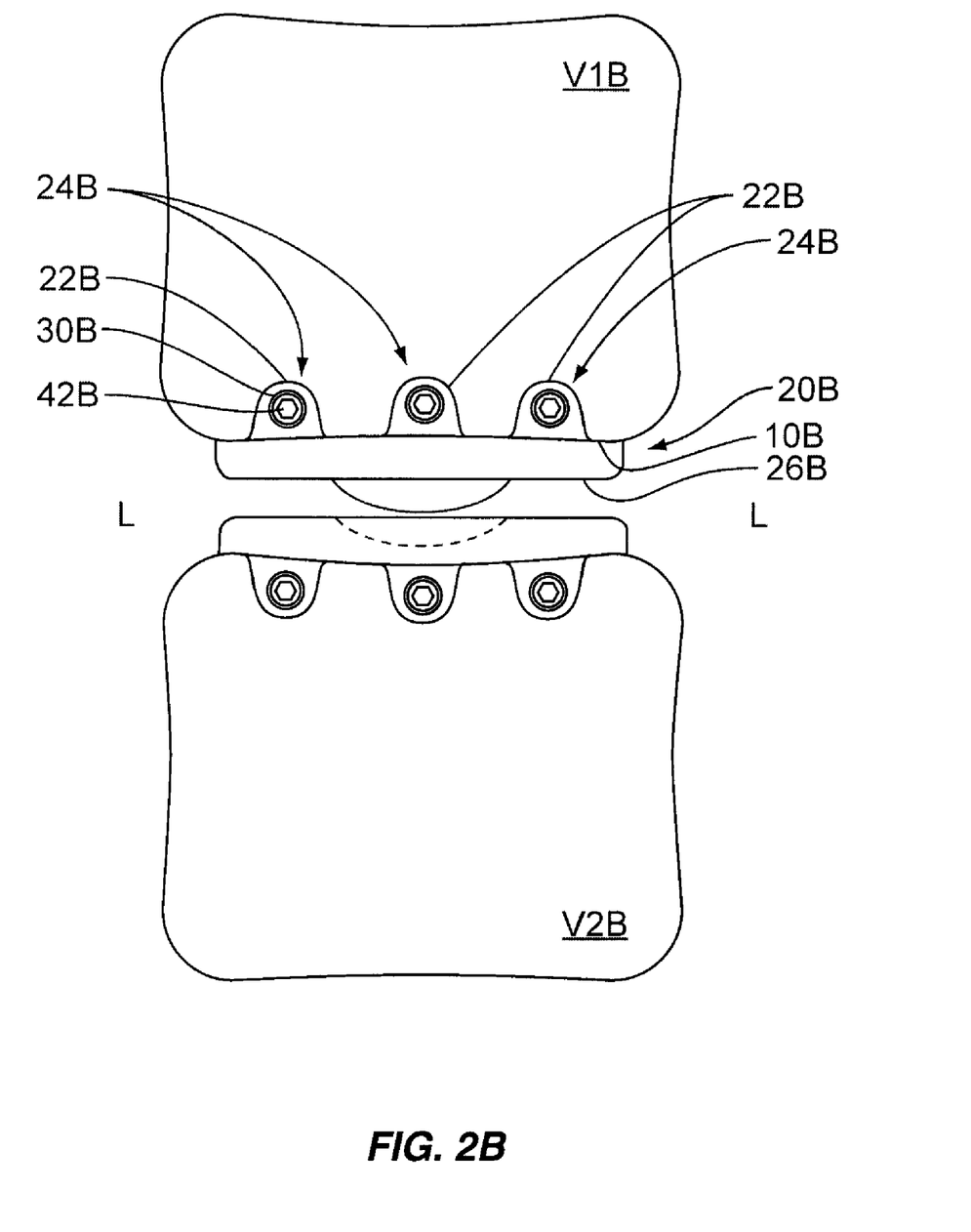
FIG. 2B is a frontal view of an alternate prosthesis of FIG. 2.

FIG. 2B shows a frontal view of an alternate prosthesis 100 of FIG. 2. This view is from the anterior side of vertebral bodies V1B and V2B, where reference marker L represents lateral sides of vertebral bodies V1B and V2B. As shown in FIG. 2B, component 20B comprises three portions 22B, each of which are situated at different areas 24B along junction 11, and the areas where portions 22B engage the vertebral body V1B are labeled by reference markers 24B. Each Portion 22B provides an area 24B for helping component 20B affix to vertebral body V1B. Further, as shown, each portion 22B comprises a fastener-receiving hole 30B for receiving a fastener. As shown in the frontal view of FIG. 2B, fastener heads 42B are visible. Similarly, as shown in FIG. 2B, the component affixed to vertebral body V2B comprises three portions for helping affix it to vertebral body V2B.

Figure 3:
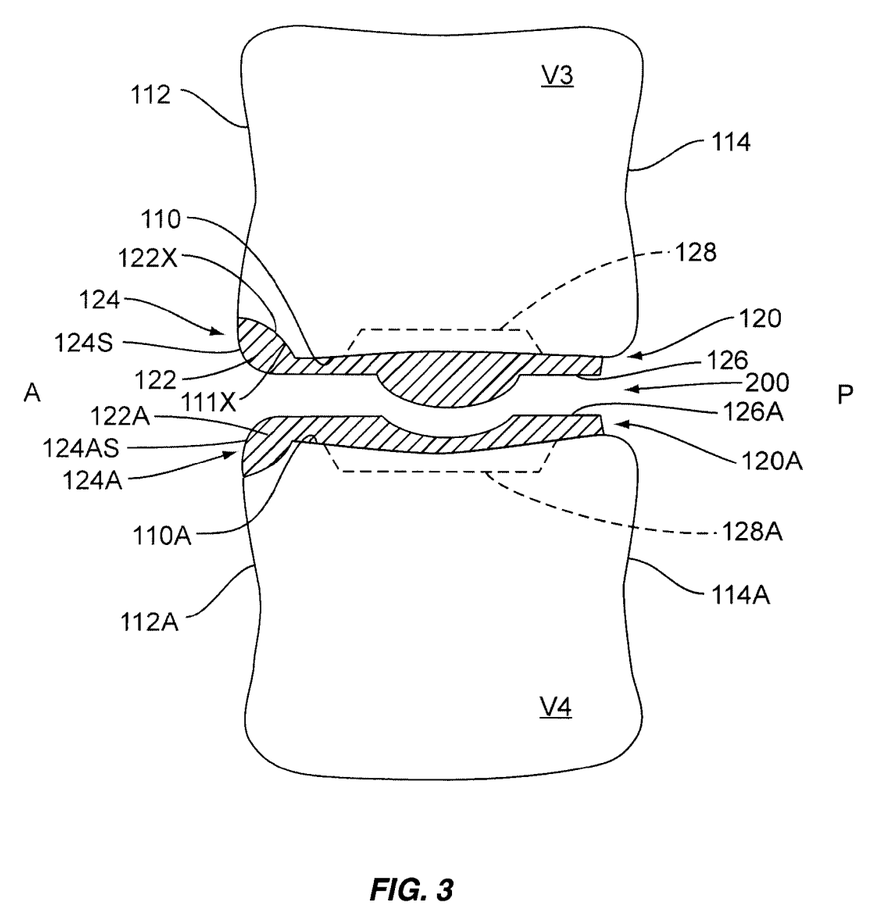
FIG. 3 is a schematic, cross-sectional view of another prosthesis in a sagittal plane.

FIG. 3 shows a schematic, cross-sectional view of a prosthesis 200 in a sagittal plane, situated primarily in the disc space 50 between vertebral bodies, labeled V3 and V4 in FIG. 3. Reference marker A represents an anterior side of the vertebral bodies V3 and V4, whereas reference marker P represents a posterior side of the vertebral bodies V3 and V4. The prosthesis 200 comprises a component 120 for engaging a surface of a vertebral body V3. The component 120 comprises a bone-engaging surface 110 and an outer surface 126 that is not bone-engaging, wherein the bone-engaging surface 110 is configured to engage a portion of the surface of the vertebral body V3, wherein the vertebral body V3 has been configured to engage with the bone-engaging surface 110. After the component 120 is engaged with the vertebral body V3, at least at a location of the area 124 of junction 11 between the vertical surface 112 and the endplate surface 110 of the vertebral body V3 (junction 11 not shown in FIG. 3, but is represented as junction 11 in FIG. 1), an outer surface 124S at area 124 of the component 120 has a shape that is substantially similar to an anatomical shape of the vertebral body V3. An anatomical shape of junction 11 is shown in FIG. 1. Note that component 120 comprises portion 122 that is situated at the location of junction 11, and the area where portion 122 engages the vertebral body V3 is labeled by reference marker 124.

Also, as shown in FIG. 3, the prosthesis 200 further comprises a component 120A for engaging a surface of a vertebral body V4. The component 120A comprises a bone-engaging surface 110A and an outer surface 126A that is not bone-engaging, wherein the bone-engaging surface 110A is configured to engage a portion of the surface of the vertebral body V4, wherein the vertebral body V4 has been configured to engage with the bone-engaging surface 110A. After the component 120A is engaged with the vertebral body V4, at least at a location of the area 124A of junction 11A between the vertical surface 112A and the endplate surface 110A of the vertebral body V4 (junction 11A not shown in FIG. 3, but is represented as junction 11A in FIG. 1), an outer surface 124AS at area 124A of the component 120A has a shape that is substantially similar to an anatomical shape of the vertebral body V4. An anatomical shape of junction 11A is shown in FIG. 1. Note that component 120A comprises portion 122A that is situated at the location of junction 11A, and the area where portion 122A engages the vertebral body V4 is labeled by reference marker 124A.

As shown in FIG. 3, area 124 of component 120 has a bone-engaging surface 122X that has a cross-sectional shape in a sagittal plane that comprises a convex shape 122X, and the vertebral body V3 has a concave shape 111X at the same area 124 to engage with surface 122X. As shown in FIG. 3, component 120A has a similar configuration at area 124A. One difference between prosthesis 200 and prosthesis 100 is that a fastener 40 or 40A are not used with prosthesis 200. Thus, there is no fastener located at areas 124 or 124A.

As shown in FIG. 3, component 120 may further comprise structures 128 to help affix component 120 to vertebral body V3. Structures 128 may be anchors, keels, spikes, pegs, prongs, or similar structures to help component 120 affix to vertebral body V3. Similarly, component 120A may further comprise structures 128A to help affix component 120A to vertebral body V4. Structures 128A may be anchors, keels, spikes, pegs, prongs, or similar structures to help component 120A affix to vertebral body V4. Surface coatings such as Hydroxyapatite (HA), plasma spray or beading also may be used instead of or in addition to respective structures 128 and 128A to help affix components to their respective vertebral bodies.

Figure 3A:
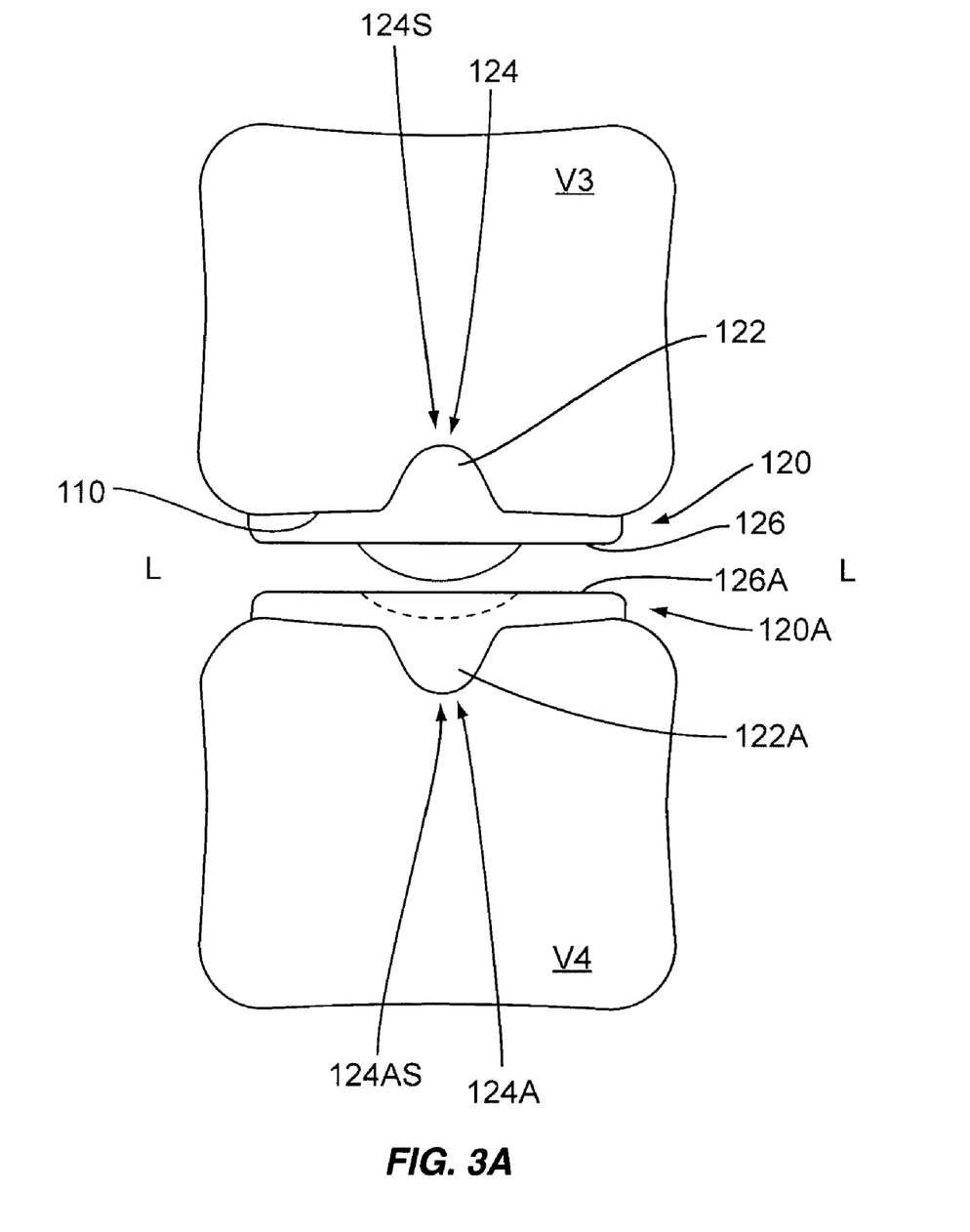
FIG. 3A is a frontal view of the prosthesis of FIG. 3, i.e., a view from the anterior side of vertebral bodies.

FIG. 3A shows a frontal view of prosthesis 200 of FIG. 3. This view is from the anterior side of vertebral bodies V3 and V4, where reference marker L represents lateral sides of vertebral bodies V3 and V4. As shown in FIG. 3A, component 120 comprises a single portion 122 that is situated at the location of junction 11, and the area where portion 122 engages the vertebral body V3 is labeled by reference marker 124. Portion 122 does provide an area 124 for helping component 120 affix to vertebral body V3, but portion 122 does not have a fastener-receiving hole for receiving a fastener. Similarly, as shown in FIG. 3A, component 120A has a similar configuration of portion 122A at location 124A.

Figure 3B:
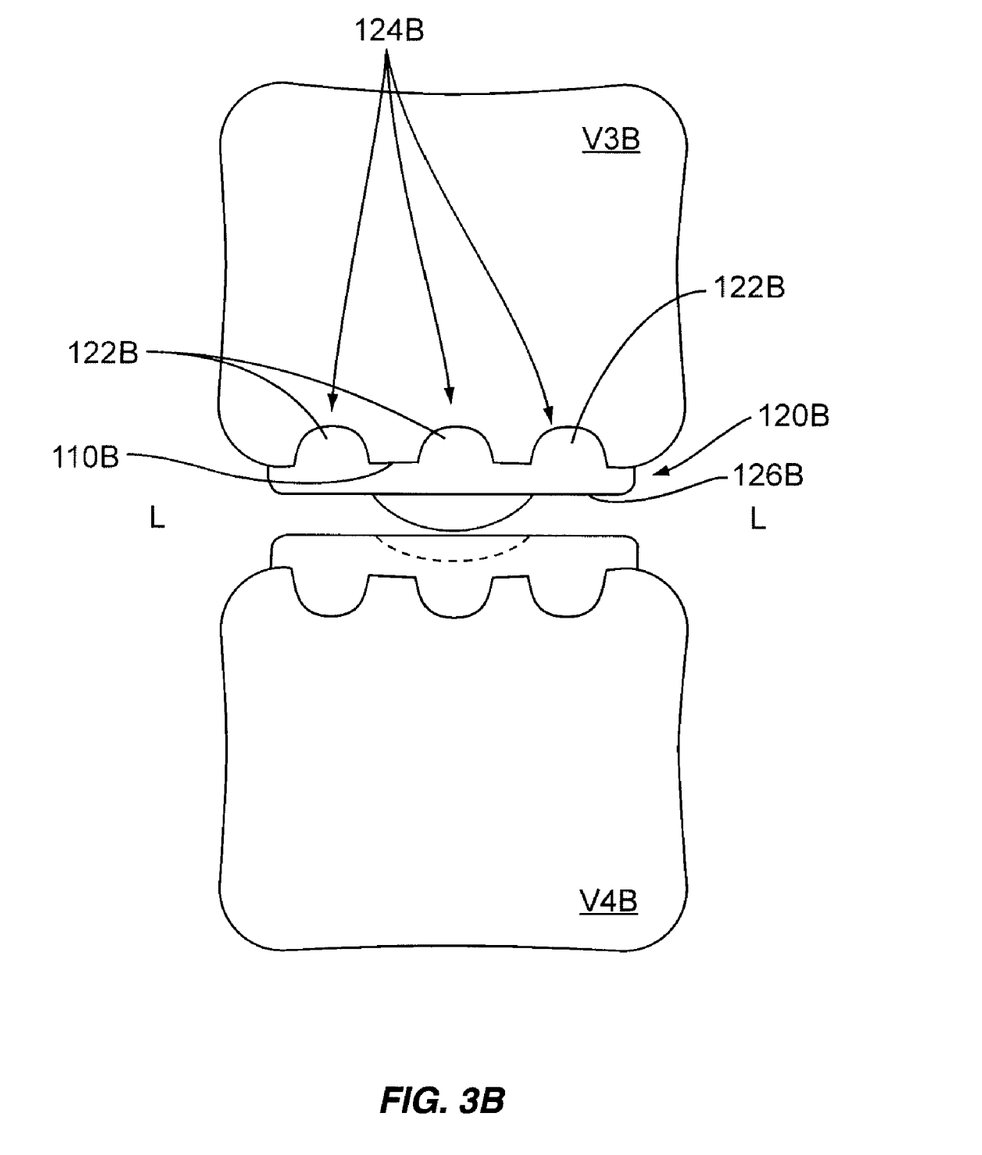
FIG. 3B is a frontal view of alternate prosthesis of FIG. 3.

FIG. 3B shows a frontal view of an alternate prosthesis 200 of FIG. 3. This view is from the anterior side of vertebral bodies V3B and V4B, where reference marker L represents lateral sides of vertebral bodies V3B and V4B. As shown in FIG. 3B, component 120B comprises three portions 122B, each of which are situated at different areas 124B along junction 11, and the areas where portions 122B engage the vertebral body V1B are labeled by reference markers 124B. Each Portion 122B provides an area 124B for helping component 120B affix to vertebral body V3B, although portions 122B do not have fastener-receiving holes. Similarly, as shown in FIG. 3B, the component affixed to vertebral body V4B comprises three portions for helping affix it to vertebral body V4B.

Figure 4:
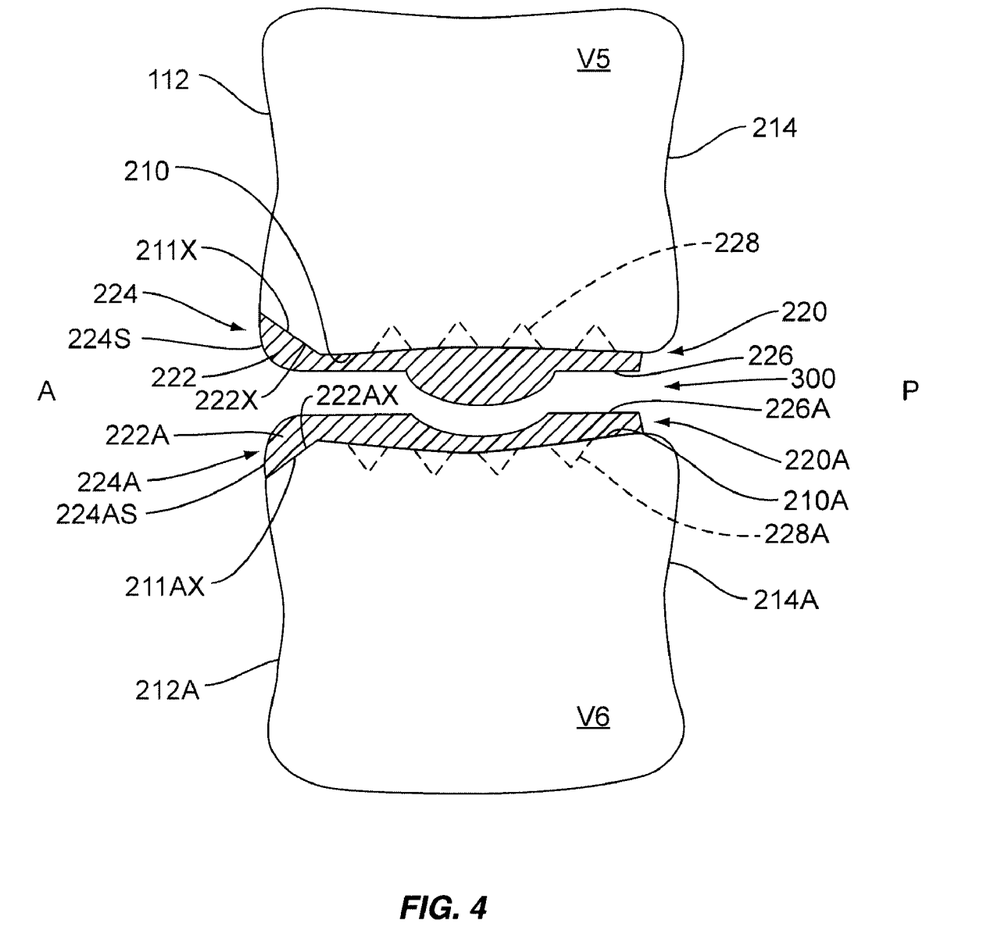
FIG. 4 is a schematic, cross-sectional view of another prosthesis in a sagittal plane.

FIG. 4 shows a schematic, cross-sectional view of a prosthesis 300 in a sagittal plane, situated primarily in the disc space 50 between vertebral bodies V5 and V6. Reference marker A represents an anterior side of the vertebral bodies V5 and V6, whereas reference marker P represents a posterior side of the vertebral bodies V5 and V6. The prosthesis 300 comprises a component 220 for engaging a surface of a vertebral body V5. The component 220 comprises a bone-engaging surface 210 and an outer surface 226 that is not bone-engaging, wherein the bone-engaging surface 210 is configured to engage a portion of the surface of the vertebral body V5, wherein the vertebral body V5 has been configured to engage with the bone-engaging surface 210. After the component 120 is engaged with the vertebral body V5, at least at a location of the area 224 of junction 11 between the vertical surface 212 and the endplate surface 210 of the vertebral body V1 (junction 11 not shown in FIG. 4, but is represented as junction 11 in FIG. 1), an outer surface 224S at area 224 of the component 220 has a shape that is substantially similar to an anatomical shape of the vertebral body V5. An anatomical shape of junction 11 is shown in FIG. 1. Note that component 220 comprises portion 222 that is situated at the location of junction 11, and the area where portion 222 engages the vertebral body V5 is labeled by reference marker 224.

As shown in FIG. 4, at the area 224 of junction 11 between the vertical surface 212 and the endplate surface 210 of the vertebral body V5, the bone-engaging surface 210 of the component 220 has a cross-sectional shape in a sagittal plane that comprises a portion of substantially zero curvature 211X, and the vertebral body V1 has a portion of substantially zero curvature 222X at the same area 224 to engage with surface 211X.

Also, as shown in FIG. 4, the prosthesis 300 further comprises a component 220A for engaging a surface of a vertebral body V6. The component 220A comprises a bone-engaging surface 210A and an outer surface 226A that is not bone-engaging, wherein the bone-engaging surface 210A is configured to engage a portion of the surface of the vertebral body V6, wherein the vertebral body V6 has been configured to engage with the bone-engaging surface 210A. After the component 220A is engaged with the vertebral body V6, at least at a location of the area 224A of junction 11A between the vertical surface 212A and the endplate surface 210A of the vertebral body V6 (junction 11A not shown in FIG. 4, but is represented as junction 11A in FIG. 1), an outer surface 224AS at area 224A of the component 220A has a shape that is substantially similar to an anatomical shape of the vertebral body V6. An anatomical shape of junction 11A is shown in FIG. 1. Note that component 220A comprises portion 222A that is situated at the location of junction 11A, and the area where portion 222A engages the vertebral body V6 is labeled by reference marker 224A.

Also, similar to component 220, as shown in FIG. 4, component 220A and vertebral body V6 have similar configurations at the area 224A of junction 11A between the vertical surface 212A and the endplate surface 210A of the vertebral body V6. That is, the bone-engaging surface 212A of the component 220A has a cross-sectional shape in a sagittal plane that comprises a portion of substantially zero curvature 211AX, and the vertebral body V6 has a portion 222AX of substantially zero curvature at the same area 224A to engage with the surface 211AX of component 220A. Note that the outer surface of component 220A at portion 222A is labeled by reference marker 224AS.

As shown in FIG. 4, component 220 may further comprise structures 228 to help affix component 220 to vertebral body V5. Structures 228 may be anchors, keels, spikes, pegs, prongs, or similar structures to help component 220 affix to vertebral body V5. Similarly, component 220A may further comprise structures 228A to help affix component 220A to vertebral body V6. Structures 228A may be anchors, keels, spikes, pegs, prongs, or similar structures to help component 220A affix to vertebral body V6. Surface coatings such as Hydroxyapatite (HA), plasma spray or beading also may be used instead of or in addition to respective structures 228 and 228A to help affix components to their respective vertebral bodies.

As with prosthesis 200 of FIG. 3, portion 222 of prosthesis 300 of FIG. 4 does provide an area 224 for helping component 220 affix to vertebral body V5, but portion 222 does not have a fastener-receiving hole for receiving a fastener. Similarly, as shown in FIG. 4, component 220A has a similar configuration of portion 222A at location 224A.

Figure 5:
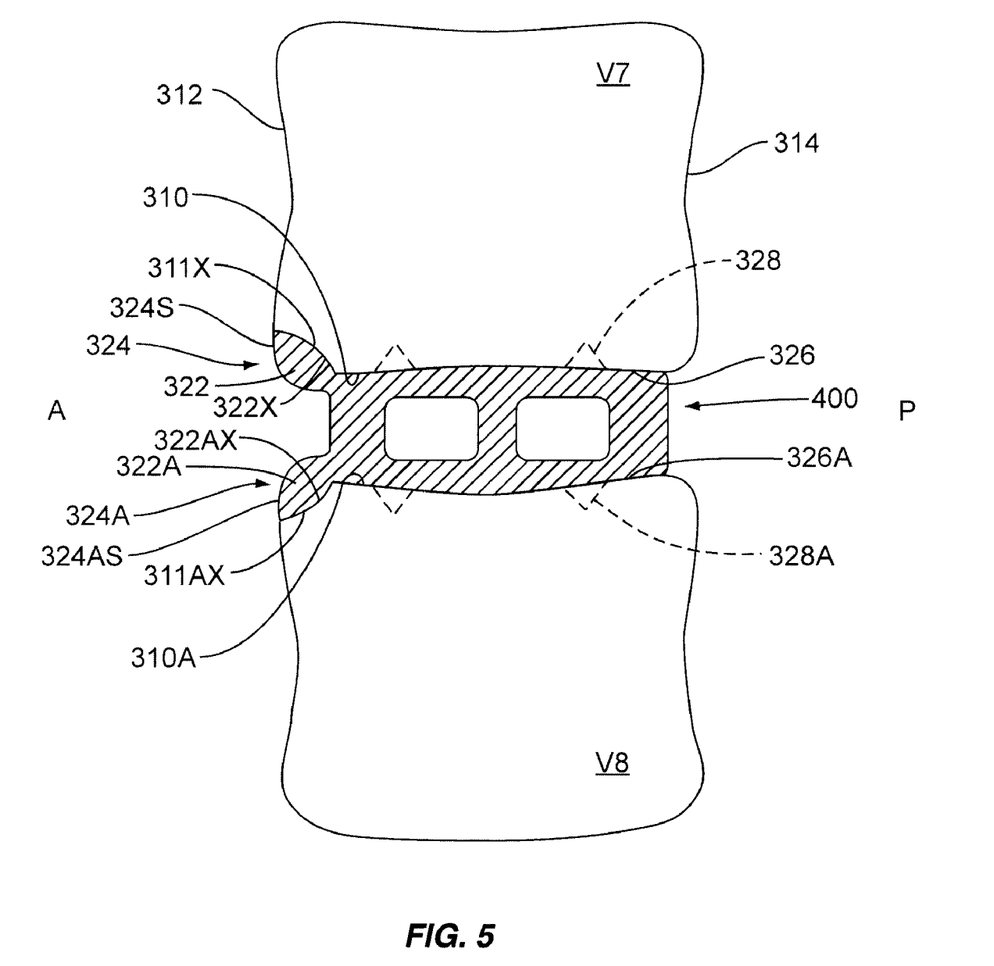
FIG. 5 is a schematic, cross-sectional view of another prosthesis in a sagittal plane.

FIG. 5 shows a schematic, cross-sectional view of a prosthesis 400 in a sagittal plane, situated primarily in the disc space 50 between vertebral bodies V5 and V6. Reference marker A represents an anterior side of the vertebral bodies V7 and V8, whereas reference marker P represents a posterior side of the vertebral bodies V7 and V8. The prosthesis 400 is an interbody fusion device comprising two bone-engaging surface 310 and 310A that are configured to engage a portion of the surface of respective vertebral bodies V7 and V8, wherein the vertebral bodies V7 and V8 have been configured to engage with the bone-engaging surfaces 310 and 310A, respectively.

After the prosthesis 400 is implanted and surfaces 310 and 310A are engaged with the vertebral body V7 and V8, at least at a location of area 324 of the junction 11 between the vertical surface 312 and the endplate surface 326 of the vertebral body V7 (junction 11 not shown in FIG. 5, but is represented as junction 11 in FIG. 1), an outer surface 324S at area 324 of prosthesis 400 has a shape that is substantially similar to an anatomical shape of the vertebral body V7. An anatomical shape of junction 11 is shown in FIG. 1. Note that prosthesis 400 comprises a portion 322 that is situated at the location of junction 11, and the area where portion 322 engages the vertebral body V7 is labeled by reference marker 224. Similarly, as shown in FIG. 5, at least at a location of area 324A of the junction 11A between the vertical surface 312A and the endplate surface 310A of the vertebral body V8 (junction 11A not shown in FIG. 5, but is represented as junction 11A in FIG. 1), an outer surface 324AS at area 324A of prosthesis 400 has a shape that is substantially similar to an anatomical shape of the vertebral body V8. An anatomical shape of junction 11A is shown in FIG. 1. Note that prosthesis 400 comprises a portion 322A that is situated at the location of junction 11A, and the area where portion 322A engages the vertebral body V8 is labeled by reference marker 324A.

As shown in FIG. 5, at the area 324 of junction 11 between the vertical surface 312 and the endplate surface 310 of the vertebral body V7, the bone-engaging surface 310 has a cross-sectional shape in a sagittal plane that comprises a convex shape 311X, and the vertebral body V7 has a concave shape 322X at the same area 324 to engage with the surface 311X. Note that the outer surface of area 324 of prosthesis 400 at portion 322 is labeled by reference marker 324S. Also, similar to surface 310, as shown in FIG. 5, surface 310A and vertebral body V8 have similar configurations at the area 324A of junction 11A between the vertical surface 312A and the endplate surface 310A. That is, the bone-engaging surface 310A has a cross-sectional shape in a sagittal plane that comprises a convex shape 311AX, and the vertebral body V8 has a concave shape 322AX at the same area 224A to engage with surface 311AX. Note that the outer surface of area 324A of prosthesis 400 at portion 322A is labeled by reference marker 324AS.

As shown in FIG. 5, bone-engaging surface 310 prosthesis 400 may further comprise structures 328 to help affix prosthesis 400 to vertebral body V7. Structures 328 may be anchors, keels, spikes, pegs, prongs, or similar structures to help prosthesis 400 affix to vertebral body V7. Similarly, bone-engaging surface 310A may further comprise structures 328A to help affix prosthesis 400 to vertebral body V8. Structures 328A may be anchors, keels, spikes, pegs, prongs, or similar structures to help component prosthesis 400 to vertebral body V8. Surface coatings such as Hydroxyapatite (HA), plasma spray or beading also may be used instead of or in addition to respective structures 328 and 328A to help affix components to their respective vertebral bodies.

All adjustments and alternatives described above are intended to be included within the scope of the invention, as defined exclusively in the following claims. Those skilled in the art also should realize that such modifications and equivalent constructions or methods do not depart from the spirit and scope of the present disclosure, and that they may make various changes, substitutions, and alterations herein without departing from the spirit and scope of the present disclosure. For example, prostheses 100, 200 and 300 are shown as motion-preserving devices, but can be modified to be fusion devices. Similarly, although all of the prostheses above are described as being configured to affix to an endplate of a vertebral body and a vertical surface of a vertebral body that is an anterior surface of a vertebral body, all of the prostheses above may be configured to affix to a posterior surface of a vertebral body, a lateral surface of a vertebral body instead of or as well as an anterior surface of a vertebral body, or any plurality or combination or such surfaces.

Furthermore, as used herein, the terms components and modules may be interchanged. It is understood that all spatial references, such as "superior," "inferior," "anterior," "posterior," "outer," "inner," and "perimeter" are for illustrative purposes only and can be varied within the scope of the disclosure.

The invention claimed is:

1. A prosthesis comprising:
   a first component comprising:
      a bone-engaging surface;
      an outer surface that is not bone-engaging; and
      a fastener-receiving hole extending through the bone-engaging surface and the outer surface;
   wherein the bone-engaging surface is configured to engage a portion of a surface of a first vertebral body, wherein the first vertebral body has been configured to engage with the bone-engaging surface, and wherein after the first component is engaged with the first vertebral body, at least at a location of an area of a junction between a vertical surface and an endplate surface of the first vertebral body, the outer surface of the first component has a shape that is substantially similar to an anatomical shape of the first vertebral body
   a second component comprising:
      a bone-engaging surface;
      an outer surface that is not bone-engaging; and
      a fastener-receiving hole extending through the bone-engaging surface and the outer surface;
   wherein the bone-engaging surface is configured to engage a portion of a surface of a second vertebral body, wherein the second vertebral body has been configured to engage with the bone-engaging surface, and wherein after the second component is engaged with the second vertebral body, at least at a location of an area of a junction between a vertical surface and an endplate surface of the second vertebral body, the outer surface of the second component has a shape that is substantially similar to an anatomical shape of the second vertebral body.

2. The prosthesis of claim 1, wherein at the area of the junction between the vertical surface and the endplate surface of the first and second vertebral body, the bone-engaging surface of each of the first and second component has a cross-sectional shape in a sagittal plane that comprises a convex shape, and wherein the vertebral body has a concave shape at the same location to engage with the outer surface.

3. The prosthesis of claim 1, wherein at the area of the junction between the vertical surface and the endplate surface of the first and second vertebral body, the bone-engaging surface of each of the first and second component has a cross-sectional shape in a sagittal plane that comprises a portion of substantially zero curvature.

4. The prosthesis of claim 1 configured so that the vertical surface of the first and second vertebral body is an anterior surface of each of the first and second vertebral body.

5. The prosthesis of claim 1 configured so that the vertical surface of the first and second vertebral body is a lateral surface of each of the first and second vertebral body.

6. The prosthesis of claim 1 configured so that the vertical surface of the first and second vertebral body is a posterior surface of each of the first and second vertebral body.

7. The prosthesis of claim 1, wherein the prosthesis is a fusion device.

8. The prosthesis of claim 1, wherein the prosthesis is a motion-preserving device.

9. The prosthesis of claim 1, wherein the fastener-receiving hole of the first and second component is positioned at the area of the junction between the vertical surface and the endplate surface of each of the first and second vertebral body, the fastener-receiving hole being configured to receive a fastener and for allowing a fastener to engage each of the first and second vertebral body.

10. The prosthesis of claim 9, wherein the fastener-receiving hole of the first and second component is configured to allow a fastener to engage each of the first and second vertebral body in a direction toward the substantial center of each of the first and second vertebral body.

11. The prosthesis of claim 9, wherein the fastener-receiving hole of the first and second component is configured so that after a fastener is inserted through the fastener-receiving hole, engages each of the first and second vertebral body, and is in its intended final position, an outer surface of a head of the fastener in combination with the outer surface of each of the first and second component has a shape that is substantially similar to an anatomical shape of each of the first and second vertebral body.

12. A prosthesis comprising:
a first component comprising:
a bone-engaging surface;
an outer surface that is not bone-engaging; and
a fastener-receiving hole extending through the bone-engaging surface and the outer surface at an area of a junction between the vertical surface and the endplate surface of a first vertebral body, the fastener-receiving hole being configured to receive a fastener and being configured to allow a fastener to engage the first vertebral body;
wherein the bone-engaging surface is configured to engage a portion of a surface of the first vertebral body, wherein the first vertebral body has been configured to engage with the bone-engaging surface; and
wherein after the component is engaged with the first vertebral body, at least at a location of the area of the junction between a vertical surface and an endplate surface of the first vertebral body, the outer surface of the first component has a shape that is substantially similar to an anatomical shape of the first vertebral body
a second component comprising:
a bone-engaging surface;
an outer surface that is not bone-engaging; and
a fastener-receiving hole extending through the bone-engaging surface and the outer surface at an area of a junction between a vertical surface and an endplate surface of a second vertebral body, the fastener-receiving hole being configured to receive a fastener and being configured to allow a fastener to engage the second vertebral body;
wherein the bone-engaging surface is configured to engage a portion of a surface of the second vertebral body, wherein the second vertebral body has been configured to engage with the bone-engaging surface; and
wherein after the second component is engaged with the second vertebral body, at least at a location of the area of the junction between the vertical surface and the endplate surface of the second vertebral body, the outer surface of the second component has a shape that is substantially similar to an anatomical shape of the second vertebral body.

13. The prosthesis of claim 12, wherein at the area of the junction between the vertical surface and the endplate surface of each of the first and second vertebral body, the bone-engaging surface of each of the first and second component has a cross-sectional shape in a sagittal plane that comprises a convex shape, and wherein each of the first and second vertebral body has a concave shape at the same location to engage with the outer surface of each of the first and second component.

14. The prosthesis of claim 12, wherein at the area of the junction between the vertical surface and the endplate surface of the first and second vertebral body, the bone-engaging surface of each of the first and second component has a cross-sectional shape in a sagittal plane that comprises a portion of substantially zero curvature.

15. The prosthesis of claim 12 configured so that the vertical surface of the first and second vertebral body is an anterior surface of each of the first and second vertebral body.

16. The prosthesis of claim 12, wherein the fastener-receiving hole of each of the first and second component is configured to allow a fastener to engage the first and second vertebral body in a direction toward the substantial center of each of the first and second vertebral body.

17. The prosthesis of claim 12, wherein the fastener-receiving hole of each of the first and second component is configured so that after a fastener is inserted through the fastener-receiving hole, engages the first and second vertebral body, and is in its intended final position, an outer surface of a head of the fastener in combination with the outer surface of each of the first and second component has a shape that is substantially similar to an anatomical shape of the first and second vertebral body.

18. A spinal prosthesis system comprising a prosthesis and a fastener, wherein:
the prosthesis comprises:

a first component for engaging a surface of a first vertebral body, the first vertebral body having a surface comprising a vertical surface and an endplate surface, the component comprising:
- a bone-engaging surface and an outer surface that is not bone-engaging;
- a fastener-receiving hole extending through the bone-engaging surface and the outer surface at an area of a junction between the vertical surface and the endplate surface of the first vertebral body, the fastener-receiving hole being configured to receive a fastener and being configured to allow a fastener to engage the first vertebral body;
- wherein the bone-engaging surface is configured to engage a portion of the surface of the first vertebral body, wherein the first vertebral body has been configured to engage with the bone-engaging surface; and
- wherein after the first component is engaged with the first vertebral body, at least at a location of the area of the junction between the vertical surface and the endplate surface of the first vertebral body, the outer surface of the first component has a shape that is substantially similar to an anatomical shape of the first vertebral body; and the fastener is configured for insertion through the fastener-receiving hole, and configured for engaging the first vertebral body, wherein when the fastener is in its intended final position, an outer surface of a head of the fastener in combination with the outer surface of the component has a shape that is substantially similar to an anatomical shape of the first vertebral body; and a second component for engaging a surface of a second vertebral body, the second vertebral body having a surface comprising a vertical surface and an endplate surface, the component comprising:
- a bone-engaging surface and an outer surface that is not bone-engaging;
- a fastener-receiving hole extending through the bone-engaging surface and the outer surface at an area of a junction between the second vertical surface and the endplate surface of the second vertebral body, the fastener-receiving hole being configured to receive a fastener and being configured to allow a fastener to engage the second vertebral body;
- wherein the bone-engaging surface is configured to engage a portion of the surface of the second vertebral body, wherein the second vertebral body has been configured to engage with the bone-engaging surface; and
- wherein after the second component is engaged with the second vertebral body, at least at a location of the area of the junction between the vertical surface and the endplate surface of the second vertebral body, the outer surface of the second component has a shape that is substantially similar to an anatomical shape of the second vertebral body; and the fastener is configured for insertion through the fastener-receiving hole, and configured for engaging the second vertebral body, wherein when the fastener is in its intended final position, an outer surface of a head of the fastener in combination with the outer surface of the second component has a shape that is substantially similar to an anatomical shape of the second vertebral body.

* * * * *